United States Patent

Nguyen

[11] Patent Number: 5,833,631
[45] Date of Patent: Nov. 10, 1998

[54] FIBER TIP GUIDEWIRE

[75] Inventor: Kim Nguyen, San Jose, Calif.

[73] Assignee: Target Therapeutics, Inc., Fremont, Calif.

[21] Appl. No.: 671,871

[22] Filed: Jun. 28, 1996

[51] Int. Cl.[6] .................................................. A61B 5/00
[52] U.S. Cl. ............................ 600/585; 600/434; 604/96; 604/202
[58] Field of Search .................. 128/772, 657, 128/658; 604/95, 96, 200, 281, 282; 600/434

[56] References Cited

U.S. PATENT DOCUMENTS

| | | |
|---|---|---|
| 3,773,034 | 11/1973 | Burns et al. . |
| 4,215,703 | 8/1980 | Willson . |
| 4,841,976 | 6/1989 | Packard et al. . |
| 5,144,959 | 9/1992 | Gambale et al. ................ 128/772 |
| 5,251,640 | 10/1993 | Osborne ............................ 128/772 |
| 5,368,048 | 11/1994 | Stoy et al. . |
| 5,385,152 | 1/1995 | Abele et al. . |
| 5,488,959 | 2/1996 | Ales . |
| 5,497,786 | 3/1996 | Urick . |

FOREIGN PATENT DOCUMENTS

| | | |
|---|---|---|
| 0382974 | 8/1990 | European Pat. Off. . |
| 0661073 | 7/1995 | European Pat. Off. . |
| WO 92/14508 | 9/1992 | WIPO . |

*Primary Examiner*—Max Hindenburg
*Assistant Examiner*—Pamela L. Wingood
*Attorney, Agent, or Firm*—Morrison & Foerster LLP

[57] ABSTRACT

This is a surgical device. In particular, it is a guidewire having a metallic core and specifically having a distal section comprising a number of fibers. The fibered distal tip is shapeable using, e.g., steam or hot air, and causes much less trauma than would a coil of similar capabilities.

14 Claims, 2 Drawing Sheets

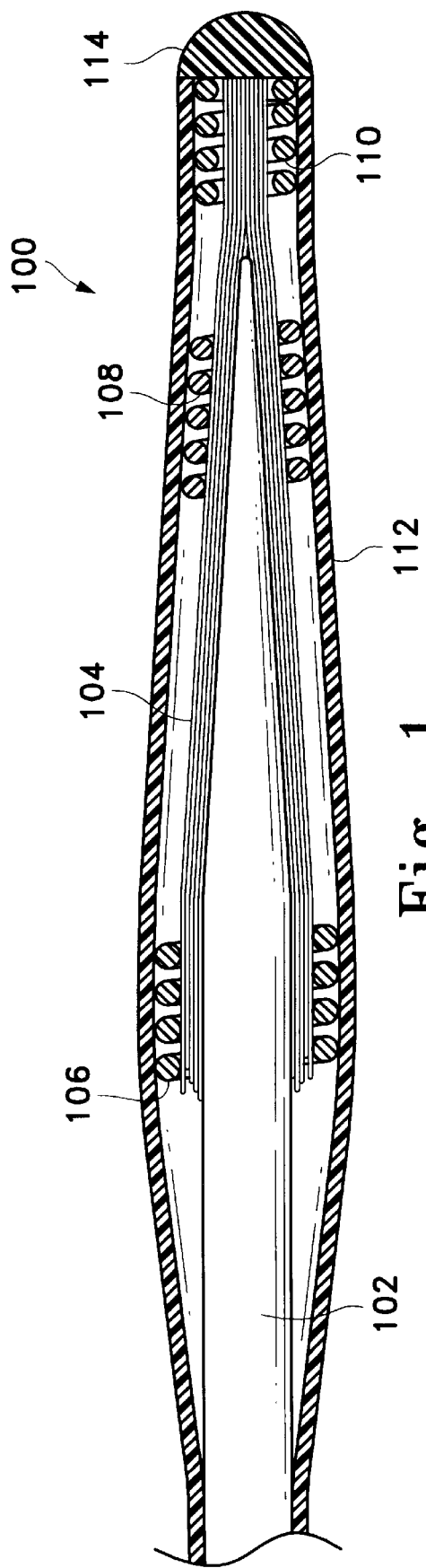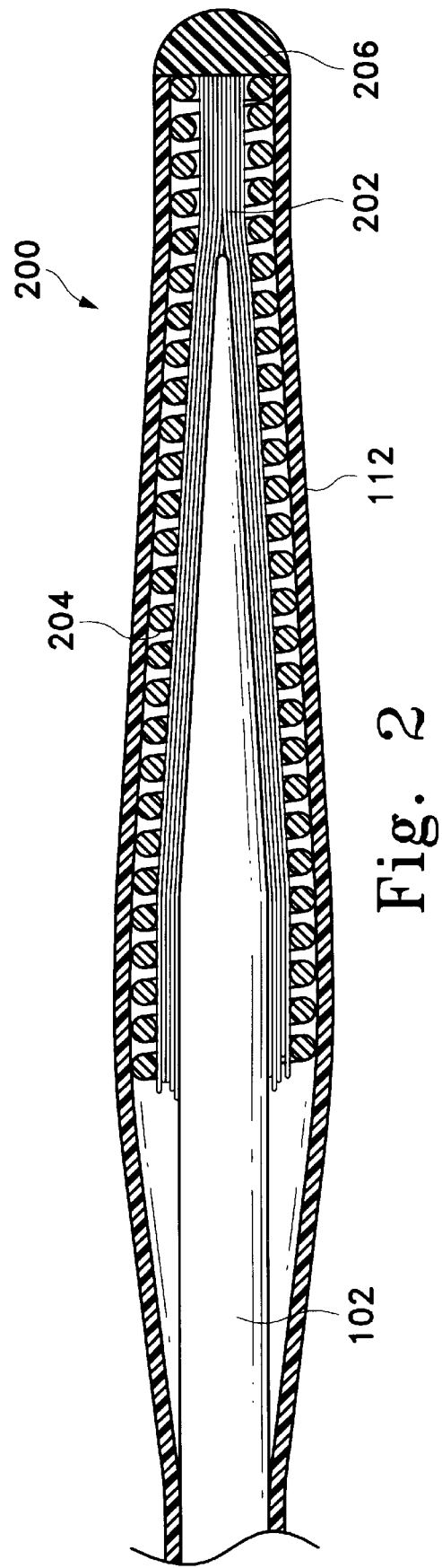

FIBER TIP GUIDEWIRE

FIELD OF THE INVENTION

This invention is a surgical device. In particular, it is a guidewire having a metallic core and specifically having a distal section comprising a bundle of fibers. The fibered distal tip is shapeable using, e.g., steam or hot air, and causes much less trauma than would a distal coil of similar capabilities.

BACKGROUND OF THE INVENTION

Catheters are used increasingly as a means for delivering diagnostic and therapeutic agents to internal sites within the human body that can be accessed through various of the body's lumen systems. Catheters are particularly useful for passage through the vasculature. The catheter guidewire is used for guiding the catheter through the bends, loops, and branches forming the blood vessels within the body. One method of using a guidewire to direct a catheter through the tortuous paths of these systems of lumen involves the use of a torqueable guidewire which is directed as a unit with the catheter from a body access point such as the femoral artery. The catheter and guidewire proceed from the femoral artery to the tissue region containing the targeted site to be treated or diagnosed. Most guidewires in use today which are used to access a site in the distal vasculature are produced of a single piece of metal or alloy such as stainless steel or superelastic nickel titanium alloys. The core is ground to form several regions of decreasing taper or smaller but constant diameter. A small collection of polymeric coverings variously used as lubricious surfaces or tie layers or stiffeners is well known. Distally, the catheter guidewire typically has a small radio-opaque coil on its distal tip to allow the attending physician using the guidewire to visualize the position of the distal tip of the guidewire with respect to the site to be treated or diagnosed. Proper use of such guidewires is a learned skill.

The distal coil, in addition to being a radio-opaque marker, provides the user with the ability to select between branches of the vasculature. That is to say that the distal coil is given a small preformed bend and, as the guidewire is twisted and pushed through the vasculature, the user is able to select one or the other branch of a branched vessel.

Shaping the coil is somewhat difficult and is also an acquired skill. Using too much force to preshape the coil before insertion in the catheter may result in a distal coil that will prolapse or bend back upon itself when finally exiting the catheter. The situation in which insufficient bending is provided to the distal tip provides a guidewire which may not be sufficiently selective when placed in tortuous distal vasculature, such as is found in the brain.

In any event, once the coil is shaped, it is difficult to reverse the set. It is further difficult to shape a distal coil end with multiple or complicated bends. Often a guidewire tip is shaped using another piece of operating room metallic equipment.

The central theme of this invention is the use of fibers at the distal tip of the guidewire. They are both less traumatic to the patient and, more importantly, they are quite easy to form into a wide variety of complicated and predictable shapes. This is so because the guidewire fiber distal tip is shaped using, e.g., a steam bath.

To our knowledge, there are no guidewires described in a prior art including a fibered tip.

Other procedures using, e.g., polymers in a form of tubing have been used on guidewires. For instance, U.S. Pat. No. 4,841,976 shows a simple guidewire having an inner tubing member made of a material such as is used to make hypodermic needles and having an outer tube made of e.g., polytetrafluoroethylene or Teflon. The inner and outer tube are connected by a "member" made of a material which is characterized as "stiff yet sufficiently flexible and able to retain a desired shape." The "member" is desirably radio-opaque. An adhesive adheres to the inner surface of the plastic covering.

A similar concept is shown in U.S. Pat. No. 5,365,048 to Stoy, et al. This patent shows a sleeved guidewire having a bendable core piece of a predetermined length and a shrinkable polymeric sleeve into which a mixture of radio-opaque metal powder and a second polymer composition which has been introduced between a tapered end of the core wire and the inner surface of the polymeric sleeve. The guidewire is characterized as being "lubricious, flexible, torqueable, sleeved... [and] with a radio-opaque tip."

U.S. Pat. No. 5,385,152 describes a steerable guidewire having an enlarged distal end portion including a soft polymeric element. The polymeric element appears to be formed of a flexible nylon polymer and has a thin hydrophilic coating of a hydrogel polymer.

U.S. Pat. No. 5,497,786 shows a guidewire having a polymer sleeve at its distal tip.

None of these documents describe or suggest a device such as is described and claimed below.

SUMMARY OF THE INVENTION

This invention is a surgical device. In particular, it is a guidewire having a metallic core and specifically having a distal section comprising a bundle of fibers. The fibered distal tip is shapeable using, e.g., steam or hot air, and causes much less trauma than would a distal coil of similar capabilities.

The fiber bundle may be made to adhere to the core wire using either or both of metallic coils and adhesives. The metallic coils may be used in any number of configurations and may also be used to provide a measure of radio-opacity to the guidewire distal tip so to allow the user to visualize the position of the guidewire using fluoroscopy.

The materials of construction are generally accepted as safe in the medical device industry, e.g., stainless steels, nickel-titanium alloys, epoxies, Dacron fibers, polyurethane tubing, and the like. Other materials are also suitable.

BRIEF DESCRIPTION OF THE DRAWINGS

FIGS. 1 through 3 are fragmentary longitudinal sectional views of guidewire tips made according to the invention.

DESCRIPTION OF THE INVENTION

Figure 3:
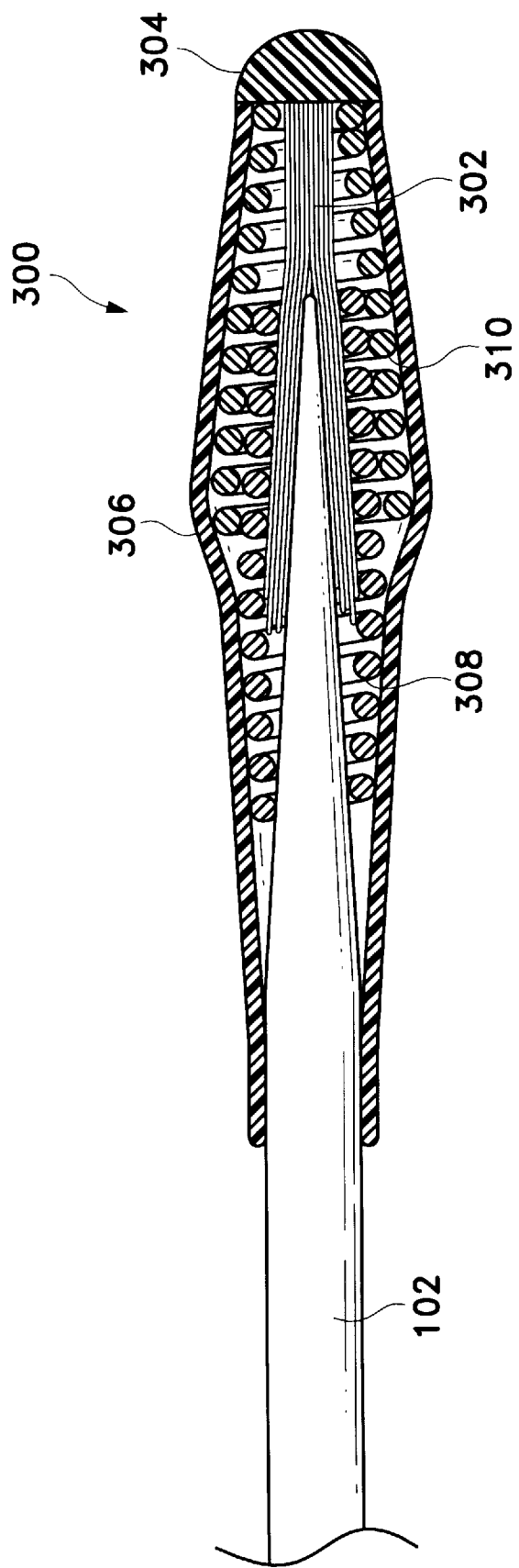

As was noted above, guidewires are used routinely in various medical procedures, typically to guide a catheter through various portions of the vasculature where a catheter cannot be expected to go by itself. The guidewires of this invention are typically used with microcatheters as may be used to access the distal vasculature of the human brain or of other organs or of peripheral sections of the body. As such, these guidewires may be of a length between 50 centimeters and 250 centimeters. The length depends, obviously, upon the site to be accessed and the size of the patient. In any case, the invention described here is one that deals with the distal portion of these guidewires. The structure of the more proximal regions of the guidewire are not important.

FIG. 1 shows one variation of the inventive guidewire (100). Centermost inside this guidewire distal tip (100) is a core wire (102). The core wire (102) may be of the materials typically used in such guidewires. Such materials include stainless steels such as SS304, SS306, SS308, SS3 10, SS3 11, SS312, and SS316. Other suitable materials include a class of materials known as super-elastic alloys, e.g., nickel-titanium alloys, and preferably those known as "nitinol" . Many useful nickel-titanium alloys also include a modest amount of an iron group metal such as chromium, cobalt, iron, etc.

Central to this invention is the presence of a multiplicity of fibrous elements (104) placed generally concentrically about the distal portion of core wire (102). In general, these fibers may extend along the exterior of the core wire (102) for a distance as long as 4 to 6 centimeters. A length of 1.5 to 2.5 centimeters is more normal. Furthermore, the fibers (104) extend for some distance distally of the core wire's (102) most distal point. These fibers are desirably polyesters such as polyethyleneterephthalete (PET) which is sold in fiber form as Dacron. Other polyesters and other polymers are also suitable for this invention. In general, it is desirable that the chosen polymers be thermoplastic or at least have some ability to be shaped using modest amounts of steam. Other known fibrous and generally suitable materials include polyethylene, polypropylene, silk, polyglycolic acid polymers, polylactic acid polymers, fluorocarbon polymers, e.g., polytetrafluoroethylene (PTFE) or the like. Other fibrous materials which may be heated so to be bent and retain a measure of softness after cooling will be apparent to those having ordinary skill in this art.

The fibers (104) are placed in a generally concentric bundle around the wire core (102). They are made to adhere to core wire (102) via the use of a combination of mechanical and/or adhesive contrivances. For instance, proximal coil (106) is shown in FIG. 1 at the proximal end of the fiber bundle (104). It may be used in conjunction with an epoxy or other adhesive to maintain the fiber bundle (104) in intimate contact with core wire (102). A secondary coil (108) is shown at the distalmost tip of the core wire (102). In addition to providing adherence of the fiber bundle (104) to core wire (102), it provides protection from inadvertent trauma from the distal tip of core wire (102) to the intima. Finally, in this variation, is a distal coil (110) which is spaced from the distal tip of core wire (102). In this instance, it should be observed that the fiber bundle (104) (and its polymeric covering (112) which is discussed with more particularity below) is all that extends between that core wire (102) distal tip and the distal coil (110). In many guidewires currently in use, the tip of a guidewire is shaped or formed pulling the distal tip of the guidewire over some hard object so to bend the distal coil. In this variation of the invention, there is no distal coil to be shaped. The shaping of the tip, that is to give it a slight curve to allow selection of branching arteries, is done by the use of heat, e.g., a steam bath.

It should be apparent to one having ordinary skill in this art that the proximal coil (106), midcoil (108) and distal coil (110) may be made of a variety of materials. They may each be polymeric or metallic. Should a polymeric material be chosen for these coils, it is desirably infused or molded with a radio-opaque filler such as powdered tantalum metal or bismuth oxide or barium sulphate or the like. Preferred, however, because of its ready availability and common usage, are radio-opaque metals such as gold, platinum, palladium and other members of the platinum group. Most preferred is an alloy of platinum and up to about 8 percent tungsten.

Finally, distal ball or tip (114) is found on the distal tip guidewire assembly (100). This tip is preferably made of a portion of fiber bundle (102) which has been heated to form the shape found in FIG. 1. Obviously, the tip (114) may be of another material such as an adhesive or epoxy.

It is highly desirable to cover the exterior of the fiber bundle (104) with a polymeric tubular covering (112). Preferably, the polymeric covering extends at least from the proximal end of the fiber bundle (104) and covers even the most distal tip (114). It is also desirable that this tubular covering (112) be of a material which can be shrunk down on and provide a measure of column strength to the fiber bundle. This exterior polymeric tubing (112) holds the fibers to the wire core (102) and provides a modest amount of stiffness to the fiber bundle extending past the distal tip of the wire core (102). Further, and depending upon the choice of materials used in the fiber bundle (104), the tubular covering (112) prevents the tip of the guidewire assembly from being thrombogenic. Many Dacron fibers have significant level of thrombogenicity which is deleterious to its function as a guidewire in the human vasculature.

Exterior polymeric covering (112) may be of a variety of different materials. For instance, it may be polyethylene or PET or polyurethane. Most preferred are soft polyurethanes. They are suitable as tie layers in that they are easily linked with hydrophilic polymers such as polyvinylpyrrolidone and polyethyleneoxide. Other hydrophilic polymers are obviously suitable in this usage.

FIG. 2 shows another variation (200) of the inventive distal guidewire tip. This variation has a core wire (102) as well. Core wire (102) is shown to be tapered to a point and to have a continuous taper throughout the length of the figure. Obviously, it may be of any suitable configuration for use with these fiber bundles. Exterior to core wire (102) is another set of fiber bundles (202). This fiber bundle (202) extends beneath a single coil (204) from a proximal region on the guidewire to well past the distal end of core wire (102). In this instance, the distal guidewire tip assembly (200) utilizes single coil (204) rather than the multiplicity of coils shown in FIG. 1. The coil is generally coextensive with fiber bundle (202). Fiber bundle (202) may form end knob (206) either with or without the outer polymeric tubing covering (112).

This variation of the invention provides for a higher level of radio-opacity than is typically achieved with the variation shown in FIG. 1. This enhanced radio-opacity is generally because of the presence of coil (204).

Adhesives may be placed at various sites along the coextension of coil (204) and fiber bundle (202) along core wire (102). The adhesive or epoxies may be used to enhance the adherence of the overall assembly to the core wire (102). An amount of that adhesive or epoxy may also be used as tip (206) or may be otherwise constructed as was discussed in relation to FIG. 1 above.

FIG. 3 shows still another variation of the inventive guidewire tip (300). In this variation, the fiber bundle (302) may overlap the core wire (102), perhaps less than is found in the two variations described above. In this variation (300), the fiber bundle (302) serves the same function as with the earlier two variations, e.g., it provides a flexible steam or heat shapeable tip which may be formed and reformed. The distal guidewire tip assembly (300) incorporates the same materials and components as discussed above, e.g., distal tip (304), outer polymeric tubular covering (306) and the like. The difference here is that it utilizes a pair of overlapping and desirably radio-opaque coils (308, 310). Coil (310) does not overlap the proximal portion of fiber bundle (302) at its proximal end. The outer coil (310) overlaps inner coil (308). These two coils (308, 310) may be used to provide a more constant diameter for the overall guidewire assembly as desired. It is an often common practice to provide a guidewire having a fairly constant diameter down into the final few distal centimeters of the device. Use of such coils is one known method for providing the means for doing so. As was noted above, these variations of the inventive device provide ways in which the distal portion of the inventive guidewire portion may be shaped without the skill of the person using the guidewire coming into play. The guidewire may be reshaped if it is given too much of a bend using a simple steaming apparatus often found in the operating theaters where such guidewires are found. The distal tip made according to this invention can be made to be quite soft and yet be of sufficient ability to select branching arteries as is the task of any good guidewire. It is simple to construct and made of materials which are readily recognized by medical device approval authorities around the world as medically safe.

The invention has been illustrated and described in detail in the drawings and foregoing description. This illustration and description is to be considered as illustrative only and not to be considered as restrictive in any manner. Any changes that come within the spirit of the invention as described are considered to be within the scope of this invention.

I claim as my invention:

1. A distal guidewire section comprising:
   a.) a metal core having a distal end, and
   b.) a multiplicity of polymeric fibers extending from a point proximal of the distal end of the metal core and extending distally to a point distal of the distal end of the metal core, said fibers being fixedly attached to said metal core at least one point.

2. The distal guidewire section of claim 1 further comprising a helical coil exterior to at least a portion of said fiber bundle.

3. The distal guidewire section of claim 2 wherein said coil extends from the distal end of the fiber bundle to a point proximal of the distal end of the metal core.

4. The distal guidewire section of claim 1 further comprising a multiplicity of helically wound coils, at least one situated distally of the distal end of the metal core, a helical coil exterior to said fiber bundle and located approximately at the distal end of the metal core.

5. The distal guidewire section of claim 4 further comprising a coil located proximally of the distal end of the metal core and exterior to the fiber bundle.

6. The distal guidewire section of claim 2 wherein the coil extends substantially the length of the fiber bundle.

7. The distal guidewire section of claim 1 further comprising a polymeric sheath extending the length of the distal guidewire section.

8. The distal guidewire section of claim 2 further comprising a polymeric sheath extending the length of the distal guidewire section.

9. The distal guidewire section of claim 1 further comprising an adhesive material adhering the multiplicity of fibers to said metal core.

10. The distal guidewire section of claim 2 further comprising an adhesive adhering the multiplicity of fibers to said metal core.

11. The distal guidewire section of claim 1, wherein said multiplicity of polymeric fibers are steam shapeable.

12. A distal guidewire section comprising:
    a metal core having a distal end; and
    a multiplicity of polymeric fibers extending from a point proximal of the distal end of the metal core and extending distally of the distal end of the metal core to provide a flexible heat formable section distal of the distal end of the metal core.

13. The distal guidewire section of claim 12, wherein said multiplicity of polymeric fibers are steam shapeable.

14. The distal guidewire section of claim 12, wherein said multiplicity of polymeric fibers are formed of a material selected from the group consisting of polyesters, polyethylene, polypropylene, silk, polyglycolic acid polymers, polylactic acid polymers and polytetrafluoroethylene.

* * * * *

UNITED STATES PATENT AND TRADEMARK OFFICE
CERTIFICATE OF CORRECTION

PATENT NO. : 5,833,631
DATED : November 10, 1998
INVENTOR(S) : Kim Nguyen

It is certified that error appears in the above-identified patent and that said Letters Patent is hereby corrected as shown below:

Column 2, line 10: please change "5,365,048" to -- 5,368,048 --.

Column 3, line 5: please change "SS3 10" to -- SS310 --.

In the Claims:
column 5, line 35,
Claim 1 at line 5: after "being" insert-- heat formable, and --.

Signed and Sealed this

Twenty-second Day of June, 1999

Attest:

Q. TODD DICKINSON

*Attesting Officer*     Acting Commissioner of Patents and Trademarks